(12) United States Patent
Jorgensen et al.

(10) Patent No.: US 9,357,801 B2
(45) Date of Patent: Jun. 7, 2016

(54) NICOTINE CHEWING GUM WITH IMPROVED UTILIZATION OF NICOTINE

(75) Inventors: Vivi Bjerre Jorgensen, Odense M (DK); My Ly Lao Stahl, Vejle Ost (DK)

(73) Assignee: Fertin Pharma A/S, Vejle (DK)

( * ) Notice: Subject to any disclaimer, the term of this patent is extended or adjusted under 35 U.S.C. 154(b) by 0 days.

(21) Appl. No.: 14/352,259

(22) PCT Filed: Oct. 19, 2011

(86) PCT No.: PCT/DK2011/000116
§ 371 (c)(1),
(2), (4) Date: Apr. 16, 2014

(87) PCT Pub. No.: WO2013/056709
PCT Pub. Date: Apr. 25, 2013

(65) Prior Publication Data
US 2014/0261505 A1    Sep. 18, 2014

(51) Int. Cl.
| | |
|---|---|
| *A24B 13/00* | (2006.01) |
| *A24B 15/10* | (2006.01) |
| *A23G 4/06* | (2006.01) |
| *A61K 9/68* | (2006.01) |
| *A24B 15/16* | (2006.01) |

(52) U.S. Cl.
CPC . *A24B 13/00* (2013.01); *A23G 4/06* (2013.01); *A23G 4/068* (2013.01); *A24B 15/16* (2013.01); *A61K 9/0058* (2013.01)

(58) Field of Classification Search
USPC ............ 131/347, 352, 270, 271; 424/48, 400, 424/440, 441; 426/3, 5; 514/161, 343
See application file for complete search history.

(56) References Cited

U.S. PATENT DOCUMENTS

| | | | |
|---|---|---|---|
| 5,488,962 A | 2/1996 | Perfetti | |
| 6,344,222 B1 | 2/2002 | Cherukuri et al. | |
| 2002/0018800 A1* | 2/2002 | Pinney et al. | 424/435 |
| 2003/0159702 A1* | 8/2003 | Lindell | A61K 31/465 |
| | | | 131/270 |
| 2004/0194793 A1* | 10/2004 | Lindell et al. | 131/270 |
| 2012/0039981 A1* | 2/2012 | Pedersen et al. | 424/440 |
| 2012/0087875 A1* | 4/2012 | Andersen et al. | 424/48 |

FOREIGN PATENT DOCUMENTS

| | | |
|---|---|---|
| WO | 02102357 A1 | 12/2002 |
| WO | 2010121619 A1 | 10/2010 |
| WO | 2010145653 A1 | 12/2010 |

OTHER PUBLICATIONS

International Search Report Application No. PCT/DK2011/000116 Completed: Jul. 4, 2012 Mailing Date: Jul. 11, 2012 3 pages.

* cited by examiner

*Primary Examiner* — Dennis Cordray
(74) *Attorney, Agent, or Firm* — St. Onge Steward Johnston and Reens, LLC

(57) ABSTRACT

The invention relates to chewing gums for the delivery of nicotine, wherein the average pH in the mouth of individuals chewing the chewing gum, in the time period from 3 to 7 minutes from the onset of chewing, is within the interval of 8.5 to 9.

25 Claims, No Drawings

NICOTINE CHEWING GUM WITH IMPROVED UTILIZATION OF NICOTINE

FIELD OF THE INVENTION

The present invention relates to the field of chewing gum. In particular, the present invention pertains to formulations and methods used to employ nicotine more efficiently from nicotine chewing gum.

BACKGROUND

Nicotine-releasing chewing gum applied for the purpose of providing a release of nicotine in a user's mouth over a certain period is well-known. Much effort has in prior art been put into emulating the nicotine release and oral perception of a cigarette when it is smoked by a user, which means that release profiles from nicotine chewing gums have been thoroughly investigated in prior art.

One of these prior art disclosures includes U.S. Pat. No. 5,488,962 specifically dealing with the problem of simulating the cigarette smoking with respect to the level of nicotine retention in the blood and saliva. According to the disclosure, an initial peak of nicotine level in the blood is obtained more similar to the corresponding absorption of nicotine when smoking a cigarette. The levels reached after a certain time corresponds to conventional nicotine chewing gums.

Another prior art disclosure is U.S. Pat. No. 6,344,222 describing a chewing gum which is claimed to provide improved release of nicotine. This improved release apparently is the result of a bi-phasic release of nicotine in initial and second doses. This document as well as most prior art is focused on how to adjust the release of nicotine from the chewing gum in order to provide plenty of nicotine for possible uptake in the body.

In short, these documents are examples of the prior art, in which focus has always been on how to adjust release of nicotine from the chewing gum; however, not much focus has been on other parameters actually controlling the uptake of nicotine from the oral saliva.

A problem with the prior art is therefore that substantial amounts of the nicotine from prior art nicotine chewing gum may be swallowed by the user and thereby transferred to the stomach whereby only a minor part of the swallowed nicotine can enter the bloodstream of the user.

Accordingly, it is an object of the present invention to improve the utilization of the nicotine from the chewing gum by facilitating an improved actual uptake of nicotine through the mucous membrane of a user.

SUMMARY OF THE INVENTION

The invention relates to a chewing gum for the delivery of nicotine, said chewing gum comprising: water-soluble chewing gum ingredients, gum base, buffer and an effective amount of nicotine in any form, wherein said chewing gum is functionally characterized in that the average saliva pH, in the time period from 3 to 7 minutes from the onset of chewing, is within the interval of 8.5 to 9, at least when the average pH is measured in 2-5 ml samples of saliva from each of ten average individuals, the average individuals being characterized by having an initial pH in the saliva of between 6.7 and 7.3 as individually measured after 1 minute of chewing on gum base free of buffer, the average individuals chewing the chewing gum at a frequency of 40 chews/minute without swallowing any saliva in the time period, and the samples being collected at 1, 3, 5, 7 and 10 minutes from the onset of chewing the chewing gum for pH-measurements within 15 minutes from obtaining the samples, the average pH being calculated for each point in time as an arithmetic mean of the individual measurements at that time, and the functional condition being fulfilled when the average pH at the points of measurement is within said interval.

It has been found by the present inventors that several surprising effects and advantages are obtained according to the invention by keeping the pH in the saliva of a user of nicotine chewing gum within the narrow interval of 8.5 to 9.0 for prolonged time periods:

Firstly, an effective amount of nicotine released from the chewing gum is absorbed by the user through the mucosa in the mouth. The alkaline pH enhances the availability of free nicotine base which is the substance able to be absorbed in this way.

Secondly, by being able to control the pH in the saliva of the chewing gum user within the aforementioned narrow boundaries for prolonged periods of time, the overall effective availability and utilization of nicotine is greatly enhanced, thereby improving the effect of the nicotine replacement therapy, namely helping the smoker to quit smoking.

Thirdly, the effective utilization of nicotine released from the chewing gum opens up for reducing the total amount of nicotine in the chewing gum, e.g. from typical 4 mg formulations to 2 mg formulations whereby the problems of side effects caused by nicotine, e.g. throat- and mouth irritation, are significantly reduced.

Furthermore, by adjusting the release of buffer to avoid pH-levels above 9, risk of irritations of the mouth and/or throat due to higher alkalinity is greatly reduced.

A nicotine chewing gum with the inventive pH-profile may be obtained in various ways which will be apparent to the skilled person. Therefore, by using a multi-variable approach involving gum base ingredients and chewing gum ingredients, chewing gum having the inventive pH-profile and at the same time having good stability and an acceptable texture may be obtained in different ways and therefore the present invention should not be limited to specific chewing gum compositions or methods of manufacture.

In an embodiment of the invention, said time period from the onset of chewing the chewing gum is 2-10 minutes, and further samples are collected and measured at least after 2 minutes from the onset of chewing.

In an embodiment of the invention, said time period from the onset of chewing the chewing gum is 1-15 minutes, and further samples are collected and measured at least after 15 minutes from the onset of chewing.

According to these embodiments of the invention the time period during which the pH is kept within the interval of 8.5 to 9 is prolonged, whereby the aforementioned effects and advantages are obtained to an even higher extent.

In an embodiment of the invention, the average pH, in the time period from 7 to 10 minutes from the onset of chewing, is within the interval of 8-9.

It has been realized by the present inventors that a comparatively stable alkaline, but not too high, pH for prolonged periods of time in the saliva in the mouth of a user of nicotine chewing gum is surprisingly important for the acceptance and effectiveness of the nicotine replacement therapy related to the use of nicotine chewing gum. It has surprisingly been found that keeping the pH below 9 while still maintaining substantial alkalinity for up to 10 minutes from the onset of chewing, improves the uptake of nicotine via the mucosa in the mouth and thereby reducing negative side effects of nicotine in the mouth and in the gastrointestinal tract. By keeping the pH below 9, sensorial acceptance of the chewing gum may be improved.

In an embodiment of the invention, the average pH, in the time period from 7 to 15 minutes from the onset of chewing, is within the interval of 8-9, further samples being collected and measured at least after 15 minutes from the onset of chewing.

In an embodiment of the invention, the average pH, in the time period from 10 to 15 minutes from the onset of chewing, is within the interval of 8-9, further samples being collected and measured at least after 15 minutes from the onset of chewing.

In an embodiment of the invention, the average pH, in the time period from 15 to 20 minutes from the onset of chewing, is within the interval of 8-9, further samples being collected and measured at least after 15 and 20 minutes from the onset of chewing.

In an embodiment of the invention, the average pH remains within an interval of less than 0.4 during 3-7 minutes from the onset of chewing the chewing gum.

In preferred embodiments of the present invention, the pH in the saliva of the user of nicotine chewing gum is kept within a narrow interval.

In an embodiment of the invention, the average pH remains within an interval of less than 0.4 during 2-10 minutes from the onset of chewing the chewing gum.

In preferred embodiments of the present invention, the pH in the saliva of the user of nicotine chewing gum is kept within a narrow interval for an extended period of time.

In an embodiment of the invention, the average pH remains within an interval of less than 0.3 during 3-7 minutes from the onset of chewing the chewing gum.

Another advantageous embodiment of the present invention has been obtained, when the average pH in the saliva of a user of the inventive nicotine chewing gum does not vary more than 0.3 while still being in the interval of 8.5-9.0 when during the time interval from 3 to 7 minutes from the onset of chewing the chewing gum.

An almost constant and relatively high pH in the saliva of the chewing gum user during chewing improves the predictability of nicotine free base concentrations in the saliva and the uptake profile of nicotine. The effective utilization of nicotine from the chewing gum may hereby be significantly improved.

In an embodiment of the invention, the accumulated release of nicotine is between 5 and 45%, preferably between 7 and 30%, more preferably between 10 and 25% by weight of the initial content of nicotine in the chewing gum after 3 minutes from the onset of chewing said chewing gum on a chewing machine as described herein.

It has been realized by the present inventors that the initial release of nicotine from a chewing gum within the first 3 minutes from the onset of chewing the chewing gum may be varied according to embodiments of the invention and still achieve a good uptake of nicotine by using the inventive pH-profile.

In an embodiment of the invention, the accumulated release of nicotine is between 10 and 55%, preferably between 15 and 45%, more preferably between 25 and 40% by weight of the initial content of nicotine in the chewing gum after 5 minutes from the onset of chewing said chewing gum on a chewing machine as described herein.

It has surprisingly been found by the present inventors that a more moderate nicotine release over time may be preferable both with respect to taste profile and utilization of the released nicotine in the bloodstream of the user. Most importantly the nicotine release over time may be adjusted to match the regulated pH in the saliva of the user whereby a synergistic effect of a more efficient absorption of nicotine via the oral mucosa may be obtained.

In an embodiment of the invention, the accumulated release of nicotine is between 30 and 85%, preferably between 40 and 80%, more preferably between 50 and 75% by weight of the initial content of nicotine in the chewing gum after 10 minutes from the onset of chewing said chewing gum on a chewing machine as described herein.

According to some embodiments of the invention, substantial amounts of nicotine are still left in the chewing gum after 10 minutes from the onset of chewing. Because the pH in the saliva at this time may still be above 8 or even above 8.5, while staying under 9.0, effective absorption of nicotine may proceed via the oral mucosa and less of the nicotine may be lost by swallowing and degradation.

In an embodiment of the invention, the accumulated release of nicotine is between 40 and 95%, preferably between 55 and 90%, more preferably between 60 and 85% by weight of the initial content of nicotine in the chewing gum after 15 minutes from the onset of chewing said chewing gum on a chewing machine as described herein.

In an embodiment of the invention, the accumulated release of nicotine is between 50 and 100%, preferably between 65 and 95%, more preferably between 750 and 90% by weight of the initial content of nicotine in the chewing gum after 20 minutes from the onset of chewing said chewing gum on a chewing machine as described herein.

In an embodiment of the invention, 0.1-0.9 mg, preferably 0.14-0.6 mg, more preferably 0.2-0.5 mg of nicotine are released after 3 minutes from the onset of chewing the chewing gum on a chewing machine as described herein, the chewing gum initially comprising 2 mg of nicotine.

In an embodiment of the invention, 0.2-1.1 mg, preferably 0.3-0.9 mg, more preferably 0.5-0.8 mg of nicotine are released after 5 minutes from the onset of chewing the chewing gum on a chewing machine as described herein, the chewing gum initially comprising 2 mg of nicotine.

Clearly, the more effectively the released nicotine is absorbed via the oral mucosa, the less initial nicotine content is necessary in the chewing gum to achieve a desired craving relief effect. According to embodiments of the present invention, the absolute release of nicotine may be adjusted in such a way that e.g. an initial content of 2 mg of nicotine in the chewing gum may actually provide a craving relief effect closer resembling the effect obtained by a prior art chewing gum with an initial nicotine content of e.g. 4 mg, whereby the amount of costly nicotine may be reduced, the taste of the chewing gum may become far more acceptable and undesired side effects resulting form high initial nicotine loadings in the chewing gum, such as irritations of throat and mouth, hiccups etc. may be greatly reduced.

In an embodiment of the invention, 0.6-1.7 mg, preferably 0.8-1.6 mg, more preferably 1.0-1.5 mg of nicotine are released after 10 minutes from the onset of chewing the chewing gum on a chewing machine as described herein, the chewing gum initially comprising 2 mg of nicotine.

In an embodiment of the invention, 0.8-1.9 mg, preferably 1.1-1.8 mg, more preferably 1.2-1.7 mg of nicotine are released after 15 minutes from the onset of chewing the chewing gum on a chewing machine as described herein, the chewing gum initially comprising 2 mg of nicotine.

In an embodiment of the invention, 1.0-2.0 mg, preferably 1.3-1.9 mg, more preferably 1.5-1.8 mg of nicotine are released after 20 minutes from the onset of chewing the chewing gum on a chewing machine as described herein, the chewing gum initially comprising 2 mg of nicotine.

In an embodiment of the invention, the chewing gum comprises glycerin in an amount of from 0.01 to 1% by weight of the chewing gum.

In an embodiment of the invention, the chewing gum comprises buffer in an amount of from 2.7 to 5.7% by weight of the chewing gum.

In an embodiment of the invention, the buffer is selected from the group consisting of a carbonate, including monocarbonate, bicarbonate and sesquicarbonate, glycerinate, phosphate, glycerophosphate, acetate, glyconate or citrate of an alkali metal, ammonium, tris buffer, amino acids and mixtures thereof.

In an embodiment of the invention, buffer is added to the chewing gum together with the water-soluble chewing gum ingredients.

When buffer is added to the chewing gum as part of the water-soluble chewing gum ingredients, a pH-profile according to embodiments of the present invention can be obtained. The release of buffer from the chewing gum into the saliva may be enhanced when the buffer, or a part of the buffer, is not mixed with the gum base during gum base manufacture. Since the gum base may tend to bind the buffer and slow down its release from the chewing gum, it may be advantageous to add buffer to the chewing gum as a separate ingredient.

In an embodiment of the invention, the gum base comprises buffer in an amount of 0.1 to 4.5% by weight of the gum base.

Buffer is necessary in the chewing gum to contribute to the desired pH-values in the saliva of a chewing gum user. Too much buffer may destabilize the chewing gum and may even help dissolving the gum base during chewing which is highly undesired. Also, according to embodiments of the present invention, pH-peaks (e.g. above 9) are not recommendable, because unwanted side effects may occur, such as mouth- and/or throat irritation.

In an embodiment of the invention, the gum base is free of buffer.

In some advantageous embodiments of the present invention, all buffers are added to the chewing gum together with the water-soluble chewing gum ingredients.

In an embodiment of the invention, the buffer comprises sodium carbonate and sodium bicarbonate in a weight-ratio between 5:1 and 2.5:1, preferably in a weight-ratio between 4.1:1 and 3.5:1.

A preferred buffer according to advantageous embodiments of the present invention is the sodium carbonate sodium bicarbonate buffer system.

In an embodiment of the invention, the chewing gum comprises gum base in an amount of from 40 to 54% by weight of the chewing gum, preferably 42 to 51% by weight of the chewing gum.

According to further embodiments of the present invention, the gum base content of the chewing gum may be varied within relatively narrow boundaries, whereby synergistic effects concerning nicotine-release, texture, pH-profile and taste may be achieved.

In an embodiment of the invention, the gum base comprises elastomers in an amount of 13 to 33% by weight of the gum base, preferably in an amount of 15 to 24% by weight of the gum base.

In an embodiment of the invention, the elastomers are selected from the group consisting of chicle gum, natural rubber, crown gum, nispero, rosidinha, jelutong, perillo, niger gutta, tunu, balata, gutta-percha, lechi capsi, sorva, gutta kay, styrene-butadiene copolymers, polyisobutylene, isobutylene-isoprene copolymers, polyethylene and combinations thereof.

In advantageous embodiments of the present invention synthetic elastomers are used to stabilize the chewing gum. Especially comparatively high molecular weight synthetic elastomers may be used e.g. to adjust the robustness of the gum base.

In an embodiment of the invention, said gum base comprises resins in an amount of 40 to 55% by weight of the gum base, preferably in an amount of 41 to 51% by weight of the gum base.

In an embodiment of the invention, the resin is selected from the group consisting of glycerol esters of partially hydrogenated rosins, glycerol esters of polymerized rosins, glycerol esters of partially dimerized rosins, glycerol esters of tally oil rosins, pentaerythritol esters of partially hydrogenated rosins, methyl esters of rosins, partially hydrogenated methyl esters of rosins pentaerythritol esters of rosins, polyvinyl acetate, terpene resins and combinations thereof.

In an embodiment of the invention, the chewing gum is free of terpene resins.

Terpene resins may unfavorably slow down the release of nicotine and also the release of buffer from the chewing gum, and in some embodiments terpene resins may therefore be avoided in the chewing gum.

In other embodiments, terpene resins, together with other gum base ingredients and chewing gum ingredients, may actively be used for release control.

In an embodiment of the invention, the nicotine is present in the form of nicotine polacrilex in an amount corresponding to 2 to 4 mg of nicotine in the chewing gum, or in the form of a nicotine salt in an amount corresponding to 2 to 4 mg of nicotine in the chewing gum, or as a combination of the two forms of nicotine corresponding to a total amount of 2 to 4 mg of nicotine in the chewing gum.

In an embodiment of the invention, said gum base comprises softeners in an amount of 8 to 20% by weight of the gum base, preferably between 12 to 18% by weight of the gum base.

In an embodiment of the invention, said softeners are selected from the group consisting of tallow, hydrogenated tallow, hydrogenated and partially hydrogenated vegetable oils, cocoa butter, degreased cocoa powder, glycerol monostearate, glycerol triacetate, lecithin, mono-, di- and triglycerides, acetylated monoglycerides, lanolin, sodium stearate, potassium stearate, glyceryl lecithin, propylene glycol monostearate, glycerine, fatty acids, petroleum wax and combinations thereof.

In an embodiment of the invention, said gum base comprises emulsifiers in an amount of 1.9 to 4.2% by weight of the gum base.

In an embodiment of the invention, the emulsifiers are selected from the group consisting of glyceryl monostearate, propylene glycol monostearate, mono- and diglycerides of edible fatty acids, lactic acid esters and acetic acid esters of mono- and diglycerides of edible fatty acids, acetylated mono and diglycerides, sugar esters of edible fatty acids, Na-, K-, Mg- and Ca-stearates, lecithin, hydroxylated lecithin and combinations thereof.

In an embodiment of the invention, the chewing gum comprises nicotine in the form of a particulate material comprising a combination of nicotine and an inorganic mineral filler, wherein nicotine is reversibly absorbed into and/or adsorbed onto the inorganic mineral filler, and wherein the BET specific surface area of the inorganic mineral filler is above 15 m²/g, the BET specific surface area measured in accordance with ISO 9277.

Particularly useful materials for absorbing nicotine and acting as nicotine supply in nicotine chewing gum are mineral filler materials having comparatively large specific surface areas.

DETAILED DESCRIPTION

The term "weight of the chewing gum" or similar wording meaning the same is defined in the present context as weight of the chewing gum, without including the weight of an outer coating, such as a hard coating, soft coating, and the like.

Chewing on a chewing machine as described herein may e.g. be carried out in accordance with European Pharmacopeia 7th. ed. 2.9.25 (Chewing gum medicated, drug release from).

Elastomers provide the rubbery, cohesive nature to the gum, which varies depending on this ingredient's chemical structure and how it may be compounded with other ingredients. Elastomers suitable for use in the gum base and gum of the present invention may include natural or synthetic types.

Elastomer plasticizers vary the firmness of the gum base. Their specificity on elastomer inter-molecular chain breaking (plasticizing) along with their varying softening points cause varying degrees of finished gum firmness and compatibility when used in base. This may be important when one wants to provide more elastomeric chain exposure to the alkane chains of the waxes.

The elastomers (rubbers) employed in the gum base may vary depending upon various factors such as the type of gum base desired, the texture of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle gum, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

Natural resins may be used according to embodiments of the present invention and may be natural rosin esters, often referred to as ester gums including as examples glycerol esters of partially hydrogenated rosins, glycerol esters of polymerised rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the resins comprise terpene resins, e.g. derived from alpha-pinene, beta-pinene, and/or d-limonene, natural terpene resins, glycerol esters of gum rosins, tall oil rosins, wood rosins or other derivatives thereof such as glycerol esters of partially hydrogenated rosins, glycerol esters of polymerized rosins, glycerol esters of partially dimerised rosins, pentaerythritol esters of partially hydrogenated rosins, methyl esters of rosins, partially hydrogenated methyl esters of rosins or pentaerythritol esters of rosins and combinations thereof.

However, in a preferred embodiment of the invention polyterpene resins may be avoided in order to optimize the pH profile and the release of nicotine.

Mixing, rolling and scoring may be done by a conventional procedure. Double sigma blade mixers are used for mixing the gum base with the other components of the formulation. The gum base may be softened in the mixer. By heat (from the heating jacket) and mixing, the gum base becomes plastic. So, the softened base is mixed with the liquid components, e g flavours, liquid sorbitol and glycerol, optionally nicotine in base form, and the solid materials, optionally nicotine in any form other than in liquid form, buffer, bulk sweetener, color as a powder mixture. The warm mass is discharged from the mixer in form of loaves stacked on trays on a truck and stored in a conditioned area until the next step starts. This is to cool the gum.

After this, the rolling and scoring takes place. The gum is extruded into a thick sheet, which is rolled by multiple sets of calender rolls to the correct thickness. The scoring rolls, usually two sets, cut the gum into the correct size.

The sheets are then transferred to a conditioned area on trays, where the sheets are cooled to make them brittle enough to be broken. The conditioned gum sheets are then broken into separate pieces of gum along the scores in the coater which is a rotating drum, prior to optionally coating the individual pieces of gum with a hard coating, soft coating or a film coating.

In an embodiment of the invention, said chewing gum ingredients are selected from the group consisting of bulk sweeteners, flavors, dry-binders, tabletting aids, anti-caking agents, emulsifiers, antioxidants, enhancers, absorption enhancers, buffers, high intensity sweeteners, colors, or any combination thereof.

In an embodiment of the invention, the chewing gum comprise one or more chewing gum ingredients selected from the group consisting of bulk sweeteners, flavors, dry-binders, tabletting aids, anti-caking agents, emulsifiers, antioxidants, enhancers, absorption enhancers, buffers, or any combination thereof.

Further useful chewing gum base components include antioxidants, e.g. butylated hydroxytoluene (BHT), butyl hydroxyanisol (BHA), propylgallate and tocopherols, and preservatives.

A gum base formulation may, in accordance with the present invention, comprise one or more softening agents e.g. sucrose esters, tallow, hydrogenated tallow, hydrogenated and partially hydrogenated vegetable oils, cocoa butter, degreased cocoa powder, glycerol monostearate, glyceryl triacetate, lecithin, mono-, di- and triglycerides, acetylated monoglycerides, lanolin, sodium stearate, potassium stearate, glyceryl lecithin, propylene glycol monostearate, glycerine, fatty acids (e.g. stearic, palmitic, oleic and linoleic acids) and combinations thereof. As used herein the term "softener" designates an ingredient, which softens the gum base or chewing gum and encompasses waxes, fats, oils, emulsifiers, surfactants and solubilisers.

To soften the gum base further and to provide it with water-binding properties, which confer to the gum base a pleasant smooth surface and reduce its adhesive properties, one or more emulsifiers is/are usually added to the composition, typically in an amount of 0 to 10% by weight, preferably 1 to 8% by weight of the gum base. Useful emulsifiers can include, but are not limited to, glyceryl monostearate, propylene glycol monostearate, mono- and diglycerides of edible fatty acids, lactic acid esters and acetic acid esters of monoand diglycerides of edible fatty acids, acetylated mono and diglycerides, sugar esters of edible fatty acids, Na-, K-, Mg- and Ca-stearates, lecithin, hydroxylated lecithin and the like and mixtures thereof are examples of conventionally used emulsifiers which can be added to the chewing gum base. The formulation may comprise certain specific emulsifiers and/or solubilisers in order to disperse and release the nicotine.

It has been found by the present inventors that chewing gums according to advantageous embodiments of the present invention should have a hardness of between 9 and 17 N, preferably 10 and 16 N, as measured with a Texture Analyser TA-XT2i from Stable Micro Systems using a needle probe 4 mm diameter cylinder stainless steel and a Flat Plate with hole (5 mm), the hardness being registered as the force required for the probe to penetrate 3.5 mm through the gum.

According to embodiments of the present invention, the obtaining of a preferred inventive pH-profile may be facilitated by establishing ideal chewing properties for the user. In this connection, chewing gums with a hardness of between 9 and 17 N, preferably 10 and 16 N, have shown to present the user with a highly inviting texture. Hereby the correct hardness may facilitate the advantageous efficient use of nicotine according to embodiments of the present invention.

In an embodiment of the invention, the chewing gum core is provided with an outer coating.

In an embodiment of the invention, said outer coating is selected from the group consisting of hard coating, soft coating and edible film-coating or any combination thereof.

According to an embodiment of the invention, at least a part of the nicotine is adhered to dry-binder particles.

According to an embodiment of the invention, an amount of dry-binder is used to adhere nicotine to bulk sweetener.

According to an embodiment of the invention, said chewing gum comprises one or more encapsulation delivery systems.

According to an embodiment of the invention, flavor may be used as taste masking for the nicotine.

The nicotine in any form according to embodiments of the invention may be selected from the group consisting of a nicotine salt, the free base form of nicotine, a nicotine derivative, such as a nicotine cation exchanger, such as nicotine polacrilex resin, a nicotine inclusion complex or nicotine in any non-covalent binding; nicotine bound to zeolites; nicotine bound to cellulose, such as microcrystalline, such as of microbial origin, or starch microspheres, and mixtures thereof.

Waxes and fats are conventionally used for the adjustment of the texture and for softening of the chewing gum base when preparing chewing gum bases. In connection with the present invention, any conventionally used and suitable type of natural and synthetic wax and fat may be used, such as for instance rice bran wax, polyethylene wax, petroleum wax (refined paraffin and microcrystalline wax), sorbitan monostearate, tallow, propylene glycol, paraffin, beeswax, carnauba wax, candelilla wax, cocoa butter, degreased cocoa powder and any suitable oil or fat, as e.g. completely or partially hydrogenated vegetable oils or completely or partially hydrogenated animal fats.

A chewing gum base formulation may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, titanium oxide, magnesium oxide, mono-, di- and tri-calcium phosphates, talc, cellulose polymers, such as wood, and combinations thereof.

According to the present invention the embodiments mentioned in the specification of this patent application may be combined to obtain further embodiments according to the present invention.

The following non-limiting examples illustrate different variations of the present invention.

EXAMPLES

Example 1

Preparation of Gum Base
Two gum bases are prepared as outlined in table 1.

TABLE 1

Gum base compositions. Amounts are given in percent by weight of each composition. GB = Gum Base

|  | GB(a) | GB(b) |
| --- | --- | --- |
| Elastomer | 22 | 15.5 |
| Synthetic and natural Resins | 43.5 | 50 |
| Filler | 16.4 | 16.4 |
| Emulsifier/Softener | 18 | 18 |
| Antioxidant | 0.1 | 0.1 |

The preparation of the gum base is carried out by first adding a high-molecular weight elastomer, resin and filler to a heated (about 120° C.) and running z-blade mixer. After about twenty minutes of mixing, more resin is added to the running mixer in further steps. After about twenty minutes of continued mixing, softeners are added to the running mixer, and mixing is continued for about five minutes before addition of further elastomer, emulsifier and antioxidant to the running mixer. Mixing is continued for about half an hour to one hour, and the final gum base mass is emptied from the mixer into coated or lined pans, extruded or cast into any desirable shape. Those skilled in the art will recognize that many variations of the above-described procedure may be followed.

Example 2

Preparation of Chewing Gum
In the present example two chewing gums are prepared with formulations as outlined in table 2. The chewing gum is prepared with NPR (nicotine polacrilex resin).

TABLE 2

Chewing gum compositions. Amounts are given in percent by weight of each composition. The chewing gum ingredients are mixed with the gum base from Example 1. CG = Chewing gum.

|  | CG(a) | CG(b) |
| --- | --- | --- |
| GB(a) | 40 |  |
| GB(b) |  | 45 |
| Filler | 14.6 | 14.6 |
| Bulk sweetener | 37.1 | 31.7 |
| High-intensity sweetener | 0.6 | 0.6 |
| $Na_2CO_3$-buffer | 4.6 | 5 |
| Flavor | 1.7 | 1.7 |
| NPR | 1.4 (15% nicotine) | 1.4 (15% nicotine) |

Example 3

In Vivo pH Profile
Table 3 shows the pH profiles over time for a number of chewing gums as well as for a commercially available chewing gum.

TABLE 3

In vivo pH measurements.

| | Time (min) | | | | | |
|---|---|---|---|---|---|---|
| | 1 | 3 | 5 | 7 | 10 | 15 |
| CG1 | 8.5 | 8.5 | 8.6 | 8.6 | 8.6 | 8.2 |
| CG2 | 9.3 | 9.3 | 9.1 | 8.5 | 7.9 | 7.4 |
| CG3 | 8.8 | 8.4 | 8.3 | 8.0 | 7.8 | N/A |
| CG4 | 9.1 | 9.0 | 9.0 | 8.7 | 8.1 | N/A |
| CG5 | 8.6 | 8.6 | 8.8 | 8.8 | 8.3 | N/A |
| CG6 | 8.6 | 8.7 | 8.9 | 8.8 | 8.5 | N/A |
| Nicorette ®, 2 mg | 7.1 | 7.7 | 7.7 | 7.7 | 7.7 | 7.6 |

The measurements of the average in vivo pH values given in Table 3 were performed as follows:

10 individuals chewed on a gum base free of buffer for 1 minute, after which the initial pH in a sample from the saliva from each of the individuals was measured with a suitable pH-electrode system, e.g. a stainless steel electrode PHW77-SS. Non of the individuals had, after chewing on a gum base free of buffer for one minute, an initial pH in the saliva outside the range from 6.7 and 7.3. The individuals thereby qualified as average individuals.

Then the 10 individuals initiated a chewing process on nicotine chewing gum containing buffer and the pH in samples from the saliva from each of the ten individuals were measured at specified time intervals. Thus each pH-value in Table 3 is the arithmetic mean of ten measurements performed on saliva-samples from ten individuals. The chewing frequency was 40 chews/minute throughout the experiment using a metronome to guide the individuals.

The sample volume of the individual saliva-samples may vary because the volume of saliva obtained may be different from each individual. This difference in sample volume does not affect the pH-measurements significantly. Also it has been established by appropriate tests that a variation in time between collection of samples does not significantly alter the result. This means that the measured pH-value after three minutes is not significantly affected by whether another saliva-sample is taken from the ten individuals e.g. after two minutes or not. Furthermore, it has been established by appropriate tests that the time from taking a sample to the time of measuring is not critical to the measured value. However, in the present measurements, the pH-values were measured in the samples within at most 15 minutes of sample collection.

In general the pH as measured in vivo for the chewing gums CG1-CG6 is seen to be higher than for the commercially available chewing gum. According to the present invention, the pH-value is preferably between 8.5 and 9.0 as long as possible during chewing.

For CG2, it is noted that the pH-value at 3 min and 5 min is actually slightly above 9.0. For such slight pH-deviations above 9.0, plasma concentration of nicotine may still be satisfying as seen below; however, these are nevertheless mainly undesired according to the present invention due to the likeliness of irritation of e.g. mucosa and throat due to the high alkaline pH-value.

It should be noted that the in vivo pH-profile is different from an in vitro pH-profile due to the fact that acidic sodium bicarbonate is normally continuously produced in saliva, hence neutralizing the alkaline contribution from buffer. Thus, the pH obtained in vivo will be lower than in vitro measured e.g. by using a chewing machine.

Example 4

Release Profiles of Nicotine

The release of nicotine from the chewing gums of example 3 was compared with a commercially available chewing gum.

TABLE 4

Release profiles. Released amounts are given in percent by weight of the initial content of nicotine. The release is measured by chewing the chewing gums in vitro on a chewing machine with 60 chews/min, in a phosphate buffer with an initial pH of 7.4.

| | Time (min) | | | | | |
|---|---|---|---|---|---|---|
| | 3 | 5 | 7 | 10 | 20 | 30 |
| CG1 | 21 | 31 | 37 | 46 | 67 | 83 |
| CG2 | 50 | 89 | 91 | 93 | 95 | 96 |
| CG3- | 16 | 27 | 34 | 41 | 63 | N/A |
| CG4- | 23 | 41 | 54 | 79 | 91 | N/A |
| CG5- | 21 | 38 | 48 | 71 | 86 | N/A |
| CG6- | 17 | 28 | 36 | 57 | 81 | N/A |
| Nicorette ®, 2 mg | 20 | 30 | 36 | 43 | 64 | 78 |

Nicotine amounts in the samples from the chewing machine were measured by a standard HPLC-method. The chewing on the chewing machine is carried out in accordance with European Pharmacopeia 7th. ed. 2.9.25.

It is seen that the release profiles of nicotine vary a lot between the disclosed chewing gums. Hereby a nicotine profile as desired may be used together with the present invention with a high pH (as seen in example 3), whereby the nicotine may be more efficiently used no matter which nicotine release profile is desired.

In particular attention should be paid to the similar nicotine release of CG1 and the prior art chewing gum. Reference will be made to this in example 5.

Example 5

Plasma Concentrations of Nicotine

The mean plasma concentrations of nicotine, corrected for predose nicotine, in the plasma obtained from blood samples from 10 individuals chewing the chewing gum, as described in example 3, were measured for two chewing gums as well as for a commercially available chewing gum.

Samples were analysed by a standard LCMS method.

TABLE 5

Mean plasma concentrations of nicotine as measured in ng/mL.

| | Time (min) | | | | | |
|---|---|---|---|---|---|---|
| | 10 | 20 | 30 | 40 | 50 | 60 |
| CG1 | 1.3 | 4.2 | 5.7 | 5.7 | 5.0 | 4.6 |
| CG2 | 2.2 | 5.2 | 5.6 | 5.2 | 4.8 | 4.7 |
| Nicorette ®, 2 mg | 0.6 | 3.0 | 4.7 | 4.8 | 4.3 | 4.4 |

For CG1 and CG2, as compared to the prior art chewing gum, a higher plasma concentration of nicotine was found throughout at least the first hour after initiating chewing of the chewing gums. As mentioned in example 4, the nicotine release over time for CG1 and the prior art chewing gum is essentially comparable, which is a clear indication that according to the present invention, a higher efficiency of the nicotine is found when having a pH-value in the range of 8.5 and 9.0, namely higher than for commercially available prior art nicotine chewing gum, but nevertheless kept in a narrow interval to avoid too high alkalinity in the mouth of the chewing gum user.

Example 6

Evaluation of Chewing Gums

In general experiments have disclosed that nicotine chewing gums, where pH in the mouth during chewing is below 8.5, result in comparatively low absorption efficiency of nicotine into the blood stream of a chewing gum user. With such low pH-value, a too large part of the nicotine is swallowed by the user instead of efficiently entering the blood system.

When pH in the mouth during chewing is above 9.0, the nicotine is used in a very efficient way. However, in vivo pH-values above 9 in the saliva of the chewing gum users are not desirable, since the highly alkaline pH-value results in problems with irritation and burning of e.g. mucosa and throat of the users.

Consequently, the chewing gums with a pH in the range between 8.5 and 9.0 are indeed suitable in that they provide an efficient utilization of nicotine and at the same time are pleasant to the user, i.e. with clearly diminished unwanted side effects when compared to chewing gum raising the pH in the saliva to above 9.

The invention claimed is:

1. Chewing gum for the delivery of nicotine, said chewing gum comprising: water-soluble chewing gum ingredients, gum base, buffer and an effective amount of nicotine in any form, wherein said chewing gum is functionally characterized in that the average pH, for the entire time period from 3 to 7 minutes from the onset of chewing, remains within the interval of 8.5 to 9, at least when the average pH is measured in 2-5 ml samples of saliva from each of ten average individuals, the average individuals being characterized by having an initial pH in the saliva of between 6.7 and 7.3 as individually measured after 1 minute of chewing on gum base free of buffer, the average individuals chewing the chewing gum at a frequency of 40 chews/minute without swallowing any saliva in the time period, and the samples being collected at 1, 3, 5, 7 and 10 minutes from the onset of chewing the chewing gum for pH-measurements within 15 minutes from obtaining the samples, the average pH being calculated for each point in time as an arithmetic mean of the individual measurements at that time, and the functional condition being fulfilled when the average pH at the points of measurement is within said interval, wherein the nicotine is present in the form of nicotine polacrilex in an amount corresponding to 2 to 4 mg of nicotine in the chewing gum, or in the form of a nicotine salt in an amount corresponding to 2 to 4 mg of nicotine in the chewing gum, or as a combination of the two forms of nicotine corresponding to a total amount of 2 to 4 mg of nicotine in the chewing gum.

2. Chewing gum according to claim 1, wherein said time period from the onset of chewing the chewing gum is 2-10 minutes, and further samples are collected and measured at least after 2 minutes from the onset of chewing.

3. Chewing gum according to claim 2, wherein the average pH, in the time period from 10-15 minutes from the onset of chewing, is within the interval of 8-9, further samples being collected and measured at least after 15 minutes from the onset of chewing.

4. Chewing gum according to claim 2, wherein the average pH does not vary more than 0.4 during 2-10 minutes from the onset of chewing the chewing gum.

5. Chewing gum according to claim 1, wherein said time period from the onset of chewing the chewing gum is 1-15 minutes, and further samples are collected and measured at least after 15 minutes from the onset of chewing.

6. Chewing gum according to claim 5, wherein the average pH, in the time period from 15 to 20 minutes from the onset of chewing, is within the interval of 8-9, further samples being collected and measured at least after 20 minutes from the onset of chewing.

7. Chewing gum according to claim 6, wherein the accumulated release of nicotine is between 50 and 100% by weight of the initial content of nicotine in the chewing gum after 20 minutes from the onset of chewing said chewing gum.

8. Chewing gum according to claim 5, wherein the accumulated release of nicotine is between 40 and 95% by weight of the initial content of nicotine in the chewing gum after 15 minutes from the onset of chewing said chewing gum.

9. Chewing gum according to claim 1, wherein the average pH, in the time period from 7 to 10 minutes from the onset of chewing, is within the interval of 8-9.

10. Chewing gum according to claim 1, wherein the average pH, in the time period from 7 to 15 minutes from the onset of chewing, is within the interval of 8-9, further samples being collected and measured at least after 15 minutes from the onset of chewing.

11. Chewing gum according to claim 1, wherein the average pH does not vary more than 0.4 during 3-7 minutes from the onset of chewing the chewing gum.

12. Chewing gum according to claim 1, wherein the average pH does not vary more than 0.3 during 3-7 minutes from the onset of chewing the chewing gum.

13. Chewing gum according to claim 1, wherein the accumulated release of nicotine is between 5 and 45% by weight of the initial content of nicotine in the chewing gum after 3 minutes from the onset of chewing said chewing gum.

14. Chewing gum according to claims 1, wherein the accumulated release of nicotine is between 10 and 55% by weight of the initial content of nicotine in the chewing gum after 5 minutes from the onset of chewing said chewing gum.

15. Chewing gum according to claim 1, wherein the accumulated release of nicotine is between 30 and 85% by weight of the initial content of nicotine in the chewing gum after 10 minutes from the onset of chewing said chewing gum.

16. Chewing gum according to claim 1, wherein the chewing gum comprises glycerin in an amount of from 0.01 to 1% by weight of the chewing gum.

17. Chewing gum according to claim 1, wherein the chewing gum comprises buffer in an amount of from 2.7 to 5.7% by weight of the chewing gum.

18. Chewing gum according to claim 1, wherein the buffer is selected from the group consisting of a carbonate, including monocarbonate, bicarbonate and sesquicarbonate, glycerinate, phosphate, glycerophosphate, acetate, glyconate or citrate of an alkali metal, ammonium, tris buffer, amino acids and mixtures thereof.

19. Chewing gum according to claim 1, wherein the buffer comprises sodium carbonate and sodium bicarbonate in a weight-ratio between 5:1 and 2.5:1.

20. Chewing gum according to claim 1, wherein the chewing gum comprises gum base in an amount of from 40 to 54% by weight of the chewing gum.

21. Chewing gum according to claim 1, wherein the gum base comprises elastomers in an amount of 13 to 33% by weight of the gum base.

22. Chewing gum according to claim 1, wherein said gum base comprises resins in an amount of 40 to 55% by weight of the gum base.

23. Chewing gum according to claim 1, wherein the chewing gum comprises nicotine in the form of a particulate material comprising a combination of nicotine and an inorganic mineral filler, wherein nicotine is reversibly absorbed into and/or adsorbed onto the inorganic mineral filler, and wherein the BET specific surface area of the inorganic mineral filler is above 15 m²/g, the BET specific surface area measured in accordance with ISO 9277.

24. Chewing gum for the delivery of nicotine, said chewing gum comprising: water-soluble chewing gum ingredients, gum base, buffer and an effective amount of nicotine in any form, wherein said chewing gum is functionally characterized in that the average pH, for the entire time period from 3 to 7 minutes from the onset of chewing, remains within the interval of 8.5 to 9, at least when the average pH is measured in 2-5 ml samples of saliva from each of ten average individuals, the average individuals being characterized by having an initial pH in the saliva of between 6.7 and 7.3 as individually measured after 1 minute of chewing on gum base free of buffer, the average individuals chewing the chewing gum at a frequency of 40 chews/minute without swallowing any saliva in the time period, and the samples being collected at 1, 3, 5, 7 and 10 minutes from the onset of chewing the chewing gum for pH-measurements within 15 minutes from obtaining the samples, the average pH being calculated for each point in time as an arithmetic mean of the individual measurements at that time, and the functional condition being fulfilled when the average pH at the points of measurement is within said interval, wherein the chewing gum comprises glycerin in an amount of from 0.01 to 1% by weight of the chewing gum.

25. Chewing gum for the delivery of nicotine, said chewing gum comprising: water-soluble chewing gum ingredients, gum base, buffer and an effective amount of nicotine in any form, wherein said chewing gum is functionally characterized in that the average pH, for the entire time period from 3 to 7 minutes from the onset of chewing, remains within the interval of 8.5 to 9, at least when the average pH is measured in 2-5 ml samples of saliva from each of ten average individuals, the average individuals being characterized by having an initial pH in the saliva of between 6.7 and 7.3 as individually measured after 1 minute of chewing on gum base free of buffer, the average individuals chewing the chewing gum at a frequency of 40 chews/minute without swallowing any saliva in the time period, and the samples being collected at 1, 3, 5, 7 and 10 minutes from the onset of chewing the chewing gum for pH-measurements within 15 minutes from obtaining the samples, the average pH being calculated for each point in time as an arithmetic mean of the individual measurements at that time, and the functional condition being fulfilled when the average pH at the points of measurement is within said interval, wherein said gum base comprises resins in an amount of 40 to 55% by weight of the gum base.

* * * * *